US009918732B2

(12) United States Patent
Flynn et al.

(10) Patent No.: US 9,918,732 B2
(45) Date of Patent: Mar. 20, 2018

(54) SACROCOLOPOPEXY IMPLANTS AND METHODS OF USING AND MANUFACTURING THEREOF

(71) Applicant: Boston Scientific Scimed, Inc., Maple Grove, MN (US)

(72) Inventors: Kenneth M. Flynn, Woburn, MA (US); Jamie Li, Lexington, MA (US); David L. Mason, Marlborough, MA (US); James M. Goddard, Pepperell, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 128 days.

(21) Appl. No.: 14/564,730

(22) Filed: Dec. 9, 2014

(65) Prior Publication Data

US 2015/0157440 A1  Jun. 11, 2015

Related U.S. Application Data

(60) Provisional application No. 61/914,112, filed on Dec. 10, 2013.

(51) Int. Cl.
  *A61F 2/00* (2006.01)
  *A61B 17/29* (2006.01)
  *A61B 17/00* (2006.01)

(52) U.S. Cl.
  CPC ............ *A61B 17/29* (2013.01); *A61F 2/0045* (2013.01); *A61B 2017/00805* (2013.01); *A61F 2220/0025* (2013.01); *A61F 2250/0007* (2013.01); *A61F 2250/0062* (2013.01)

(58) Field of Classification Search
  CPC ............ A61F 2/0045; A61F 2220/0025; A61F 2250/0062; A61F 2250/0007; A61B 2017/00805; A61B 17/29
  See application file for complete search history.

(56) References Cited

U.S. PATENT DOCUMENTS

| 4,300,268 | A  | * | 11/1981 | Wilson ...................... B42F 1/08 24/547 |
|---|---|---|---|---|
| 7,306,131 | B2 | * | 12/2007 | Bargo ................... B25C 5/0228 227/110 |
| 9,713,518 | B2 |   | 7/2017 | Kennet et al. |
| 2004/0039246 | A1 | * | 2/2004 | Gellman ............... A61F 2/0036 600/30 |
| 2009/0259094 | A1 | * | 10/2009 | Bouchier .............. A61F 2/0045 600/37 |
| 2010/0174134 | A1 | * | 7/2010 | Anderson ........ A61B 17/06109 600/37 |
| 2010/0261950 | A1 | * | 10/2010 | Lund ..................... A61F 2/0045 600/30 |
| 2010/0312052 | A1 | * | 12/2010 | Morningstar ........... A61F 2/004 600/40 |

(Continued)

*Primary Examiner* — Christine H Matthews
*Assistant Examiner* — Joshua D Lannu
(74) *Attorney, Agent, or Firm* — Brake Hughes Bellermann LLP

(57) ABSTRACT

Some embodiments are directed to medical devices, and methods for making and using the medical devices. An exemplary medical device includes a first elongate member, a second elongate member, and a coupler. The coupler may be configured to removably couple the first elongate member to the second elongate member.

18 Claims, 16 Drawing Sheets

(56) References Cited

U.S. PATENT DOCUMENTS

2010/0331612 A1* 12/2010 Lashinski .......... A61B 17/0401
                                                      600/37
2011/0137340 A1*  6/2011 Cummins .......... A61B 17/0644
                                                      606/219

* cited by examiner

SACROCOLOPOPEXY IMPLANTS AND METHODS OF USING AND MANUFACTURING THEREOF

CROSS-REFERENCE TO RELATED APPLICATION

This application is a Nonprovisional of, and claims priority to, U.S. Patent Application No. 61/914,112, filed on Dec. 10, 2013, entitled "SACROCOLOPOPEXY IMPLANTS AND METHODS OF USING AND MANUFACTURING THEREOF", which is incorporated by reference herein in its entirety.

TECHNICAL FIELD

The disclosed invention relates generally to medical devices, implants, methods of manufacturing the devices and implants, and methods for delivering implants within a pelvic region of a patient to treat various pelvic dysfunctions. More particularly, the disclosed invention relates to sacrocolopopexy mesh implants to treat prolapse of pelvic organs.

BACKGROUND

A variety of medical procedures are performed to treat various female pelvic dysfunctions, including procedures to treat urinary incontinence, and correcting various pelvic organ prolapse (POP) conditions, such as, uterine prolapse, cystoceles, rectoceles, and vaginal vault prolapse. A cystoceles occurs when the bladder bulges into the vagina; a rectoceles occurs when the rectum bulges into the vagina; a hysterocele occurs when the uterus descends into the vagina; and an enterocele (small bowel prolapse) occurs when the small bowel pushes through the upper wall of the vagina.

The existing procedures for treating POP usually include implanting pelvic implants within a variety of different anatomical structures within a pelvic region. For example, some sacrocolopopexy procedures involve delivering and securing a mesh to support the vagina by affixing it to tissue near the sacrum of the patient. Physicians may purchase rectangular mesh sheets from which they cut shapes as per their objectives for the procedure. A Y-shaped mesh implant may also be used for treating the POP. The Y-shaped mesh implant may reduce the time required to cut and assemble mesh during the procedure. However, some physicians may still continue to buy mesh sheets to create their own implants because it gives them flexibility to separately position and adjust two mesh pieces, which may be a limitation with the Y-shaped mesh. Therefore, there exists a need for ready-made mesh implants that may be implanted in the body of the patient without lengthy customizing and thus, avoiding consumption of extra time and efforts.

SUMMARY

The present disclosure provides alternative medical devices as well as methods for manufacturing and using the alternative medical devices that addresses one or more of the above mentioned issues.

One illustrative embodiment discloses a medical device having a first elongate member, a second elongate member, and a coupler. The coupler may removably couple the first elongate member to the second elongate member.

Another illustrative embodiment discloses a method for placing a medical device into a body of a patient. The medical device may include a first elongate member, a second elongate member, and a coupler. The method may include attaching a first end portion of the first elongate member to a vagina of the patient. A second end portion of the first elongate member may be attached to a sacrum of the patient. The second elongate member may be attached to the vagina of the patient and may be coupled to the first elongate member using the coupler.

Yet another illustrative embodiment discloses a delivery tool. The delivery tool may include an elongate body, a first arm, a second arm, and an actuator. The first and second arms may extend from the elongate body. The first arm may be configured to removably retain a first member of a coupling device, while the second arm may be configured to removably retain a second member of the coupling device. The actuator may be configured to move the first arm with respect to the second arm.

The above summary of some embodiments is not intended to describe each disclosed embodiment or every implementation of the present disclosure. The Figures, and Detailed Description, which follow, more particularly exemplify these embodiments, but are also intended as exemplary and not limiting.

BRIEF DESCRIPTION OF THE DRAWINGS

The disclosure may be more completely understood in consideration of the following detailed description of various embodiments in connection with the accompanying drawings.

DETAILED DESCRIPTION

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings, in which similar elements in different drawings are identified with the same reference numbers. The drawings, which are not necessarily to scale, depict illustrative embodiments and are not intended to limit the scope of the disclosure.

Figure 1:
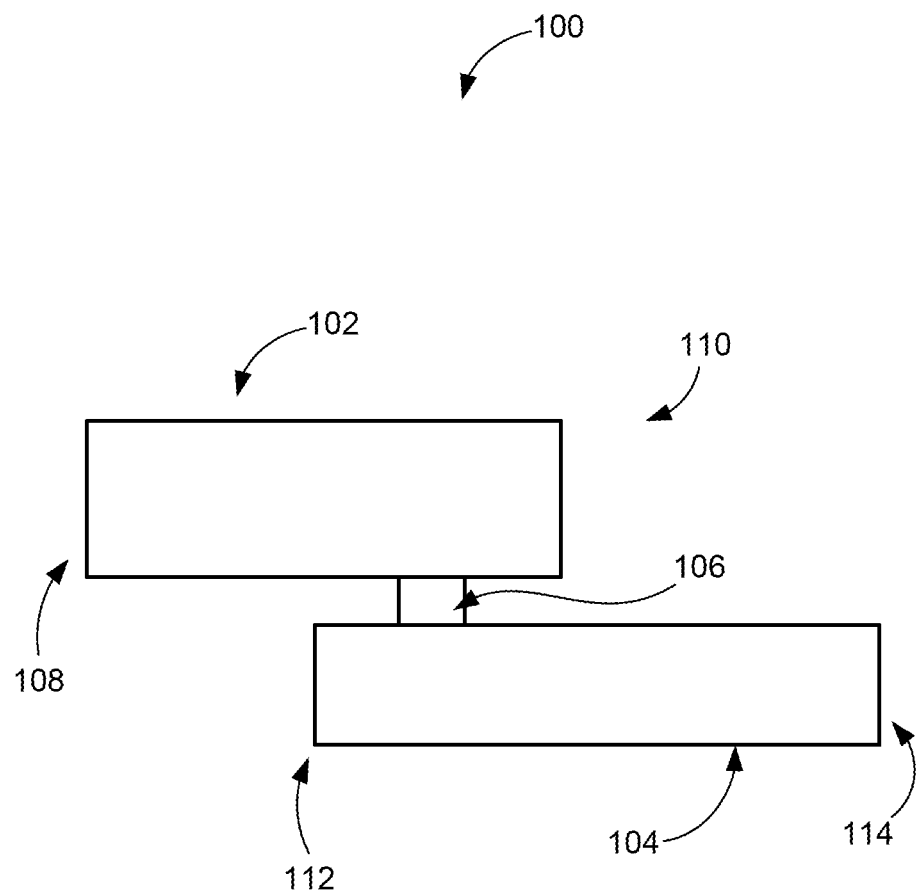
FIG. 1 is a schematic view of a medical device, according to an embodiment of the invention.

FIG. 1 schematically illustrates a medical device 100, according to an embodiment of the invention. The medical device 100 can be implanted within a body of a patient to correct or help correct POP (pelvic organ prolapse). The medical device 100 includes a first elongate member 102, a second elongate member 104, and a coupler 106. The first elongate member 102 may include a first end portion 108, and a second end portion 110. Similarly, the second elongate member 104 may include a first end portion 112, and a second end portion 114. In some embodiments, the first elongate member 102 may be longer than the second elongate member 104 so that the first elongate member 102 can be provided to connect or extend from anterior wall of the vagina with the sacrum or tissue proximate the sacrum of the patient, and the second elongate member 104 may be coupled to the posterior wall of the vagina, or vice versa. The first elongate member 102 may provide support to posterior wall of the vagina, while the second elongate member 104 may provide support to anterior wall of the vagina, which will be discussed in conjunction with subsequent figures.

The coupler 106 may be provided to removably couple the second elongate member 104 with the first elongate member 102. The coupler 106 may be employed to produce a desired tension in the elongate members 102, 104, and can be detached if the elongate members 102, 104 are loosely connected, for example, to the vagina or between the vagina and the sacrum. Examples of the coupler 106 may include, but are not limited to a clip, a pin, a snap fastener, or any other suitable fastener, or the like that can be used to couple the first elongate member 102 with the second elongate member 104.

In some embodiments, the coupler 106 may be detachably attached to the elongate members so that in case desired tension is not produced in the elongate members connecting the vaginal walls with the sacrum, the coupler 106 may be detached and reattached to the elongate members thereby providing a tight grasp on coupling the elongate members. In some embodiments, the coupler 106 may be temporarily fixed to the elongate members. When the desired tension is achieved in the elongate members, a suture or any other fixation member can be tied down to the elongate members, thereby permanently fixing the elongate members with the vaginal walls. Thereafter, the coupler 106 may be removed. Hence, the coupler 106 may be permanently or temporarily attached to the elongated members.

In some embodiments, the invention described herein may be used to place any device, such as an implantable mesh, into a body of a patient and allow for adjustability. Details of attaching the medical device 100 within the vagina will be discussed in conjunction with subsequent figures.

Figure 2:
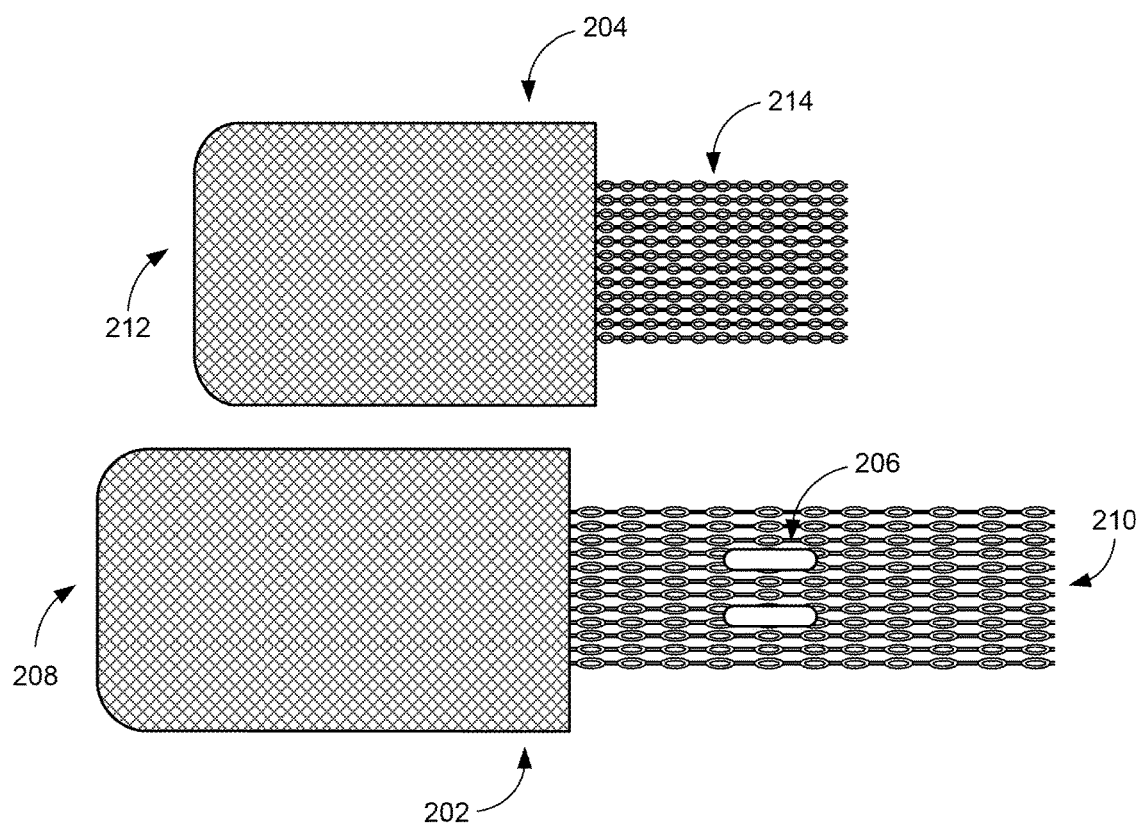
FIG. 2 is a top view of a medical device according to an embodiment of the invention.

Now turning to FIG. 2, a medical device 200 may include elongate members 202, 204. Each of the elongate members 202, 204 may be a mesh. The mesh may include a number of interconnected strands or woven strands, such that pores are formed between the adjacent strands. Alternatively, the mesh may be formed of a sheet material comprising pores through the thickness of the material. The mesh may be formed or made from any biocompatible material. For example, the mesh may be made from suitable elastic or non-elastic, biocompatible materials so that the mesh may not break when tension is produced in the mesh and the tension is retained by the coupler 206. Materials used for the mesh may be natural or synthetic. Examples of such materials may include, but are not limited to, polymers, such as, polyester, silk, nylon, polydioxinone, polygylcolic acid, polyvinylidene fluoride, etc.; natural grafts, such as, porcine dermis, small intestinal submucosa, etc. In some embodiments, the mesh may be made from a monofilament macroporous polypropylene.

Figure 3:
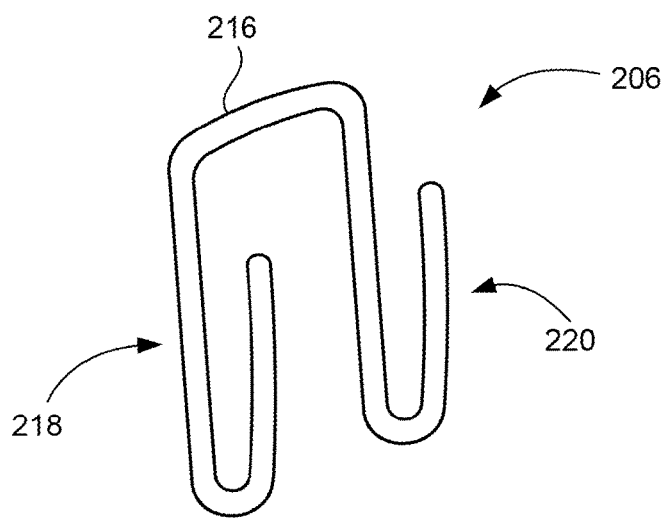
FIG. 3 is a perspective view of a coupler of the medical device of FIG. 2.
Figure 4:
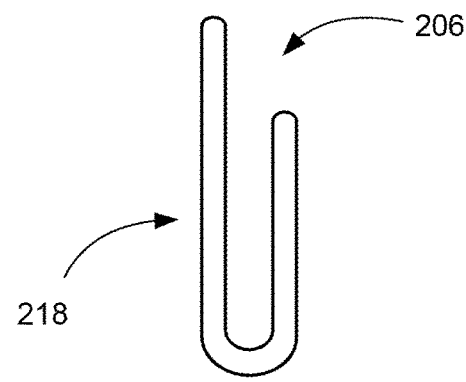
FIG. 4 is a side view of the coupler of FIG. 3.
Figure 5:
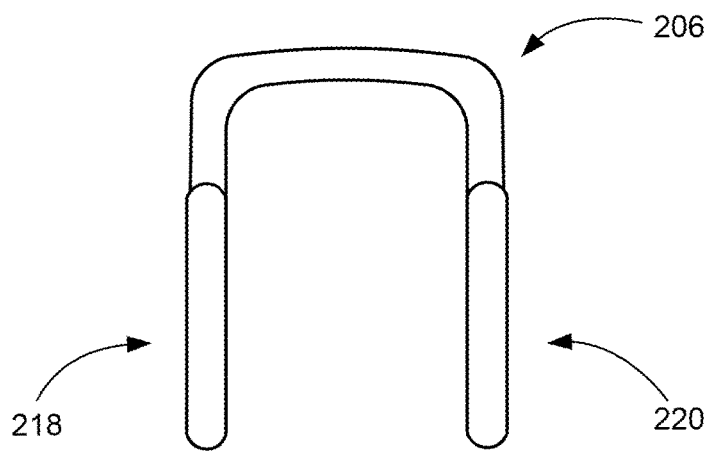
FIG. 5 is a front view of the coupler of FIG. 3.

FIG. 3 is a perspective view of a coupler 206 of the medical device 200 of FIG. 2. The coupler 206 may include a body portion 216 that is an elongated body. In some embodiments, the body portion 216 may be tubular, cylindrical, or the like. The coupler 206 may also include a first extension portion 218, and a second extension portion 220. Each of the extension portions 218, 220 may be positioned on either side of the body portion 216. Each of the extension portions 218, 220 may be configured to extend at an angle from the longitudinal axis of the body, and in some embodiments perpendicularly from the body portion 216 and form a non-linear, hook-like, or bent shape, for example a U-shape, as referenced by 218a and 220a in FIG. 3 respectively. For example, the extension portions may each include three sections that collectively form a U-shape. A side view of the coupler 206 is shown in FIG. 4. FIG. 5 shows a front view of the coupler 206.

The coupler 206 may be made of any biocompatible material in total or in portions. For example, the coupler 206 may be made from various suitable biocompatible materials having suitable tensile strength to engage and hold or couple the elongate members 202, 204 to one another. Examples of such materials may include, but are not limited to, metals, alloys, polymers, and combinations thereof. Examples of the metals may include gold, silver, platinum, titanium, nickel, aluminum, and so forth. Examples of the alloys may include stainless steel, nitinol, and so forth. Examples of the polymers may include polypropylene, polyvinylidene fluoride, nylon, poly ether ether ketone (PEEK), polycarbonate and so forth.

Figure 6:
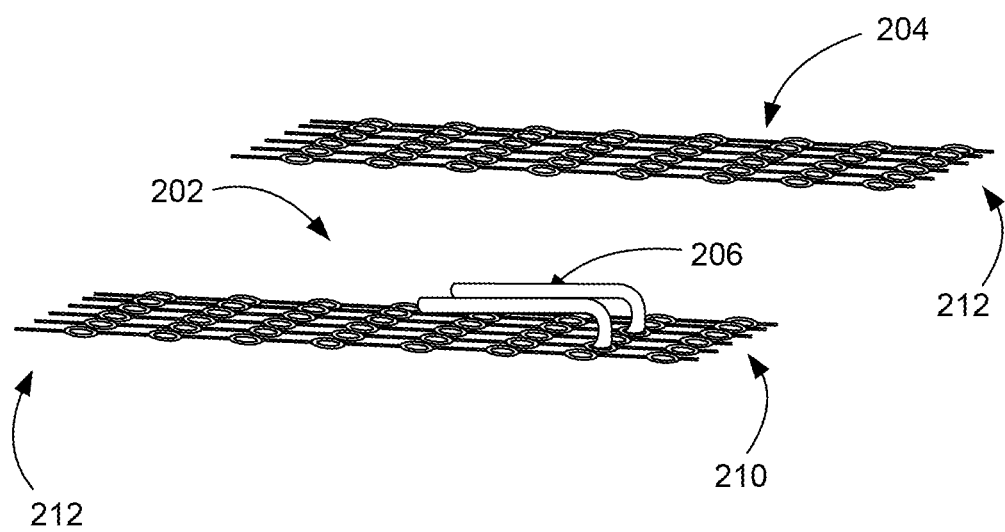
FIGS. 6 and 7 are perspective views of a medical device according to an embodiment of the invention.
Figure 7:
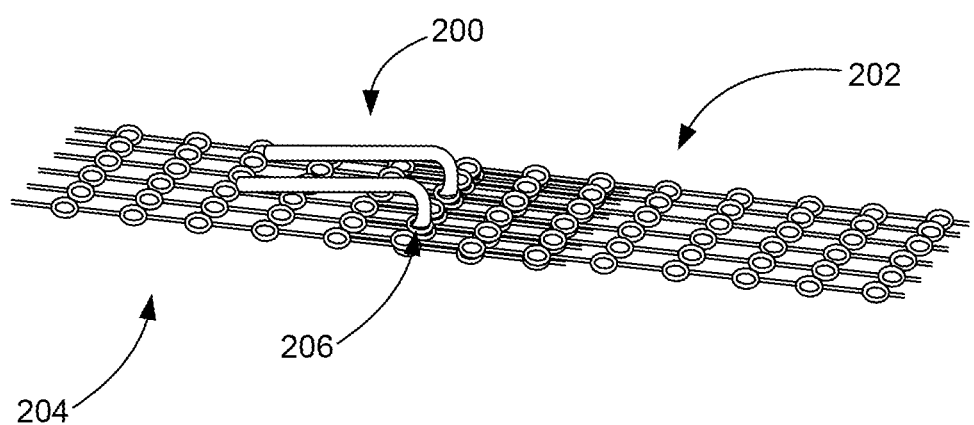

In some embodiments, the coupler 206 may be attached to the second end portion 210 of the first elongate member 202, as shown in FIG. 6. In order to attach the coupler 206 with the second end portion 210, the coupler 206 may firstly be placed underneath (or adjacent a face or side of) the second end portion 210, followed by allowing the extension portions 218, 220 to emerge from the pores of the mesh of the first elongate member 202. Extension portions 218 and 220 may be flexible, such that they may bend to insert through the pores and then bend back to an initial position where they may grab the mesh. Then, the first end portion 212 of the second elongate member 204 may be placed over the extension portions 218, 220 and moved such that the extension portions 218, 220 emerge from the pores of the mesh of the second elongate member 204, as shown in FIG. 7. This way, the coupler 206 couples or connects the second elongate member 204 with the first elongate member 202.

Figure 8:
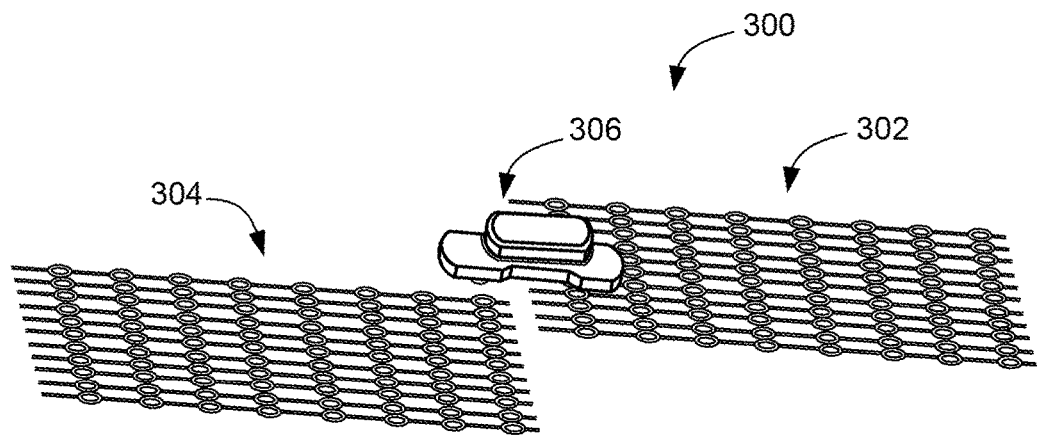
FIGS. 8 and 9 are perspective views of a medical device according to an embodiment of the invention.
Figure 9:
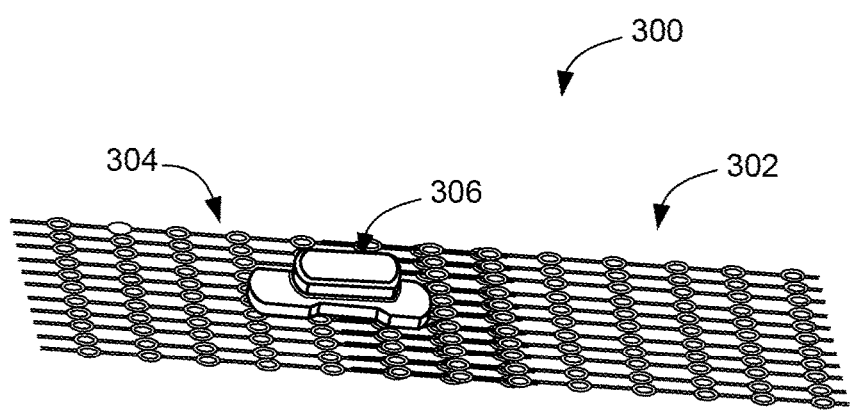
Figure 10:
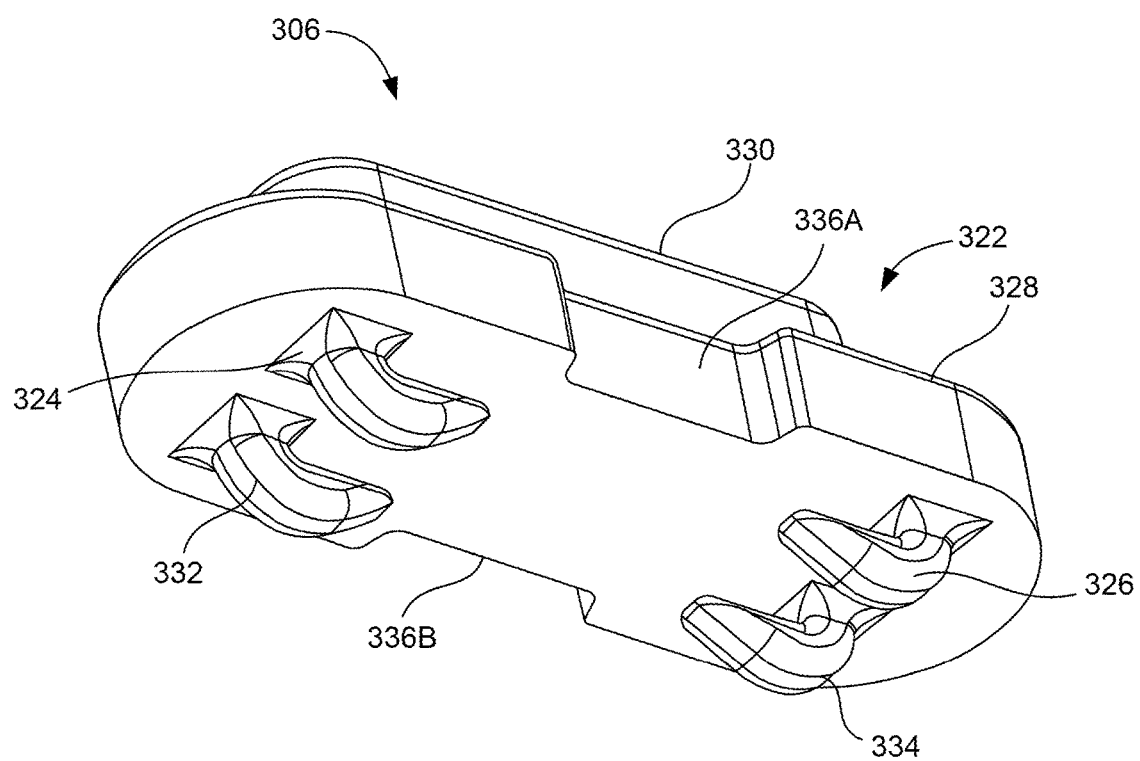
FIG. 10 is a perspective view of a coupler of the medical devices of FIGS. 8 and 9.

FIGS. 8 and 9 illustrate another exemplary embodiment of a medical device 300. In some embodiments, the medical device 300 may include a first elongate member 302, and a second elongate member 304, which are structurally and functionally similar to the first elongate member 102, and the second elongate member 104 respectively of FIG. 1. The medical device 300 also includes a coupler 306 having a body portion 322, a first barb member 324, and a second barb member 326. The body portion 322 may include a substantially flat or flat elongated surface 328 that extends to form a projection or extension portion 330 on the flat elongated surface 328 as shown in FIG. 10. The term 'flat elongated surface 328' will be referred as 'flat surface 328' hereinafter. The body portion 322 may include or define cut outs 336A and 336B on its edges or sides. The cut outs 336A and 336B may provide a surface for grasping the coupler 306 by a physician. The projection 330 may have a small diameter or size as compared to the diameter or size of the flat surface 328, thereby providing an ergonomic grip on the coupler 306 while deploying the coupler 306 on the elongate members 302, 304. The flat surface 328 and the projection 330 may have a shape that is substantially elliptical. It will be appreciated, however, that other shapes are also suitable for the flat surface 328 and the projection 330, such as, but not limited to, oblong, semi-circular, conical, square, or the like. Each of the corners of the flat surface 328 and the projection 330 may be rounded so that damage to body tissue may be reduced, thereby ensuring safety during both deployment and usage. Barb members may be designed to minimize the chance for irritating or perforating tissue. In some embodiments, barbs are flexible and can bend to detach from the mesh to adjust the mesh length, then bend back after reattaching through the mesh to avoid having pointed ends facing tissue.

Further, on an underside of the body portion 322, the barb members 324, 326 are positioned opposite to each other. The first barb member 324 may extend towards the second barb member 326, and the second barb member 326 may extend towards the first barb member 324. In some embodiments, the barb members face directly opposite each other, while in other embodiments, the barb members face opposite each other, but off axis from one another.

In some embodiments, more than one barb member may be provided beneath the flat surface 328. As shown in FIGS. 10, 11, 12A, 12B, and 12C, there are four barb members, i.e., the first barb member 324, the second barb member 326, a third barb member 332, and a fourth barb member 334. In the illustrated embodiment, the first barb member 324 and the third barb member 332 are positioned adjacent and may be parallel to each other. Likewise, the second barb member 326 and the fourth barb member 334 are positioned adjacent and parallel to each other. Further, the first barb member 324 may be extended towards the second barb member 326, and vice versa. Similarly, the third barb member 332 may be extended towards the fourth barb member 334, and vice versa. Each of the barb members 324, 326, 332, and 334 may be configured to twist to form a crook or hook-type shape for engaging the barb members 324, 326, 332, and 334 with the elongate members 302, 304, as shown in FIGS. 8 and 9. As shown in FIG. 8, the barb member, such as the first barb member 324 (in case there are two barb members positioned opposite to each other) may be engaged with the mesh of the first elongate member 302, such that the crook shape of the first barb member 324 may be tucked into or extend through the pore at a first end portion 308 of the first elongate member 302. The crook-shaped first barb member 324 may tuck into or extend through the pore at a second end portion 314 of the second elongate member 304 when the second end portion 314 is placed beneath the engaged first end portion 308. Further, the crook shaped barb member 326 may tuck into any pore of the mesh of the second elongate member 304, thereby coupling the first elongate member 302 with the second elongate member 304, as shown in FIG. 9. Any of these barbs may be flexible to allow for attachment to the mesh while maintaining a low profile when the barb is in its relaxed state. In some embodiments, the least number of barbs necessary is 2, facing relatively opposite one another, but any number more than 2 also may be utilized.

Turning back to FIGS. 10, 11, 12A, 12B, and 12C, the first barb member 324 and the third barb member 332 may extend through the pores at of the first elongate member 302, and into the pores at the second end portion 314 of the second elongate member 304 placed beneath the first end portion 308 of the first elongate member 302. Further, the second barb member 326 and the fourth barb member 334 can tuck or fix into any available pores at the second elongate member 304. In the above embodiments, the second barb member 326 or the second barb member 326 and the fourth barb member 334 can be tucked into the pores of the second elongate member 304 with respect to the position of the engaged pores of the first elongate member 302 such that desired tension is produced in the elongate members 302, 304.

Figure 12A:
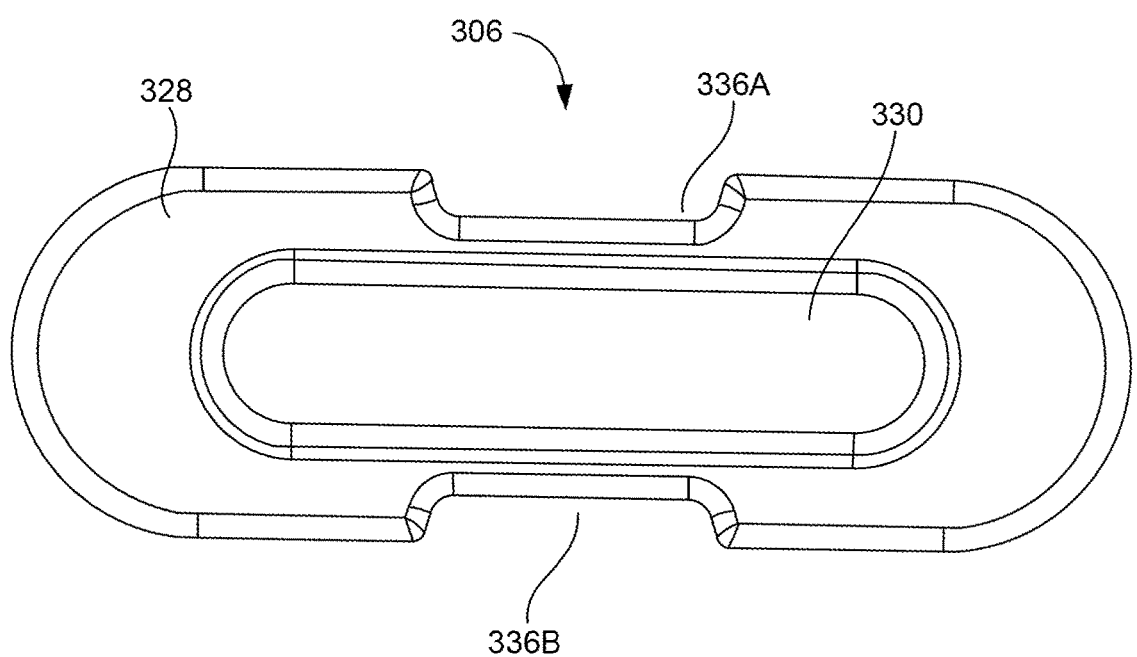
FIG. 12A is a top view of the coupler of FIG. 10.

As best illustrated in FIG. 12A, the projection 330 is concentric with the flat surface 328. Alternatively, the projection 330 may not be concentric and may be offset with respect to the flat surface 328. The projection 330 may have a smaller diameter than the diameter of the flat surface 328.

Figure 11:
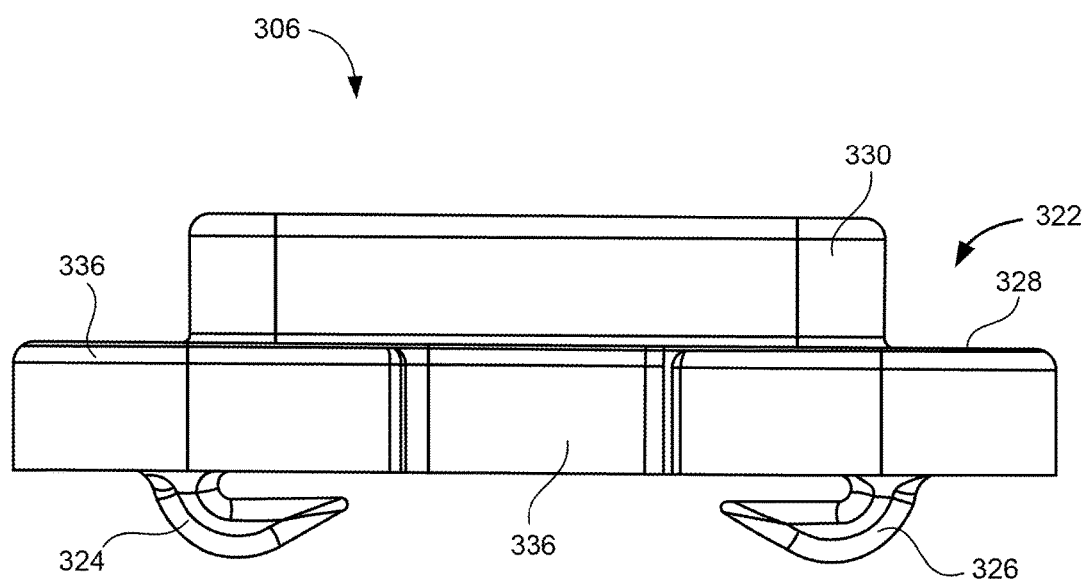
FIG. 11 is a side view of the coupler of FIG. 10.
Figure 12B:
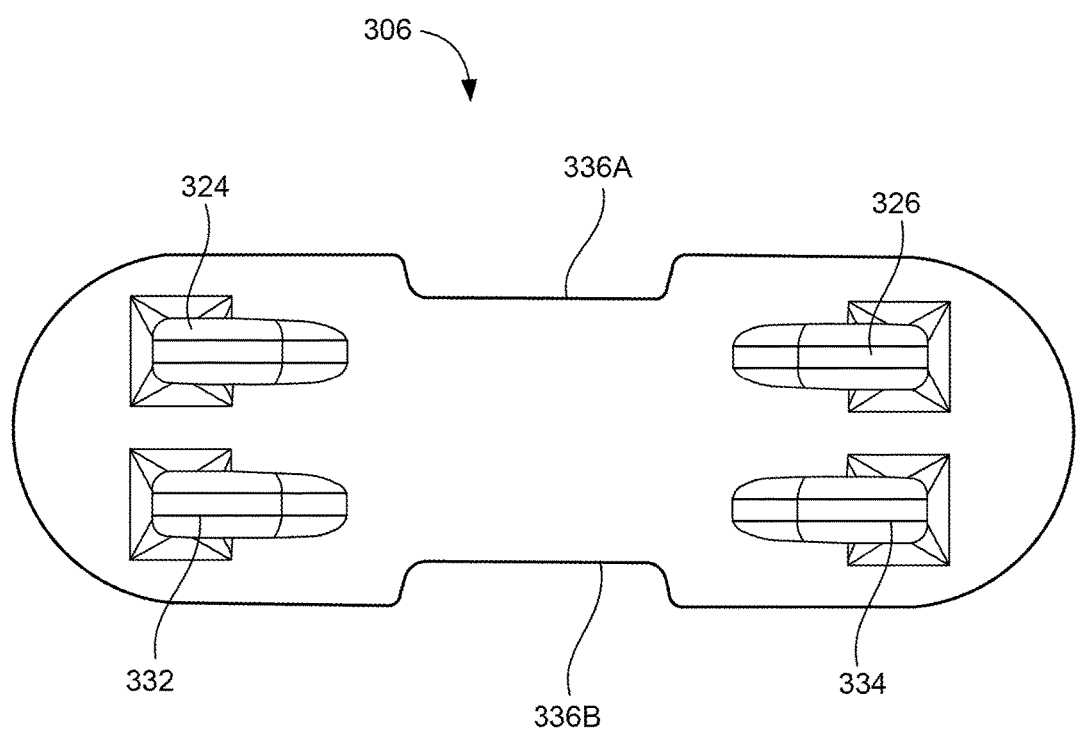
FIG. 12B is a bottom view of the coupler of FIG. 10.
Figure 12C:
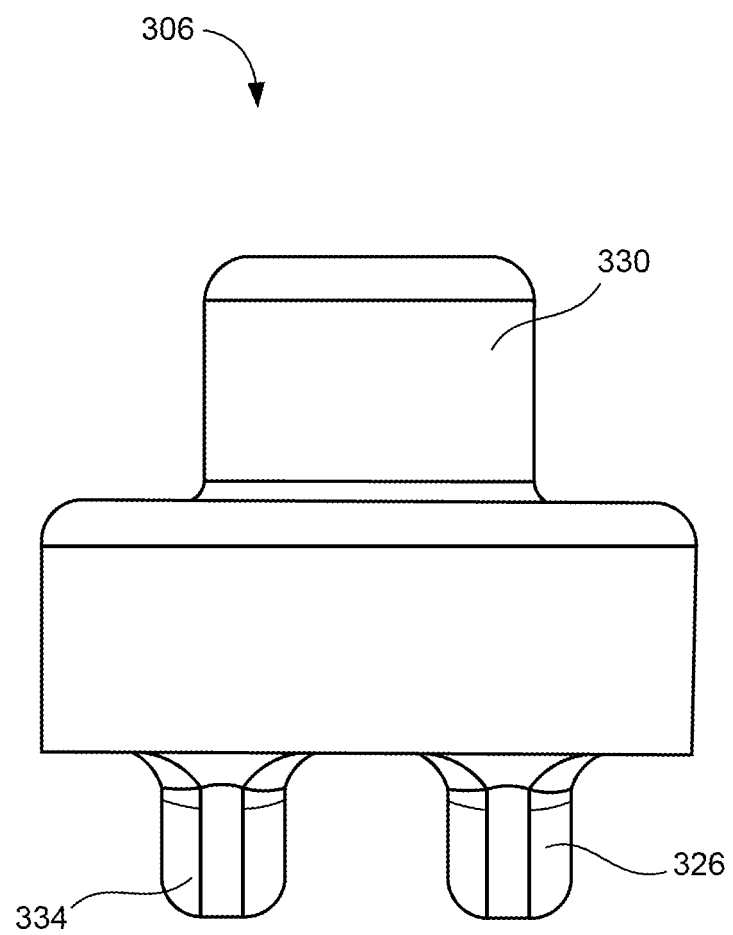
FIG. 12C is a side view of the coupler of FIG. 10.

As best illustrated in FIGS. 11 and 12B, the barb members 324, 326, 332, 334 are disposed below the flat surface 328.

In some embodiments, the coupler may be a snap fastener, as shown in FIGS. 13-16. In this illustrated embodiment, a medical device 400 may include a first elongate member 402, a second elongate member 404, and a coupler 406. The elongate members 402, 404 may be similar in structures and functionality to the elongate members 102, 104 of FIG. 1, respectively.

Figure 14:
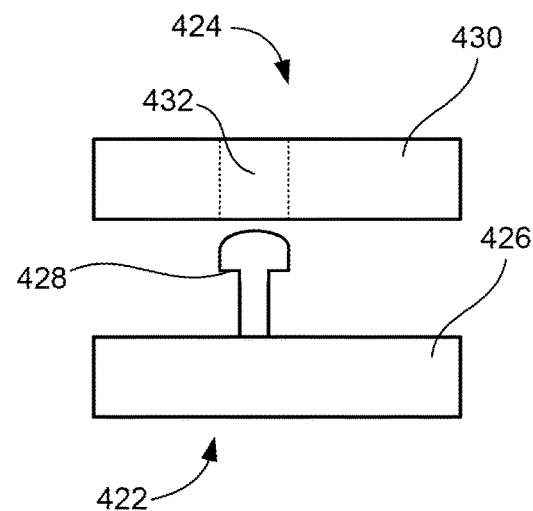
FIG. 14 is a side view of a coupler of the medical device of FIG. 13.
Figure 15:
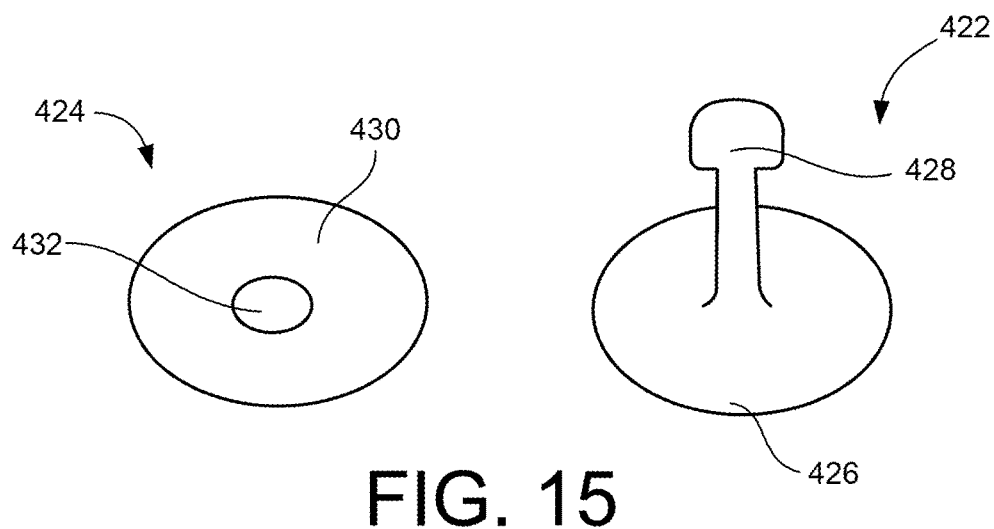
FIG. 15 is a perspective view of the coupler of the medical device of FIG. 13.
Figure 16:
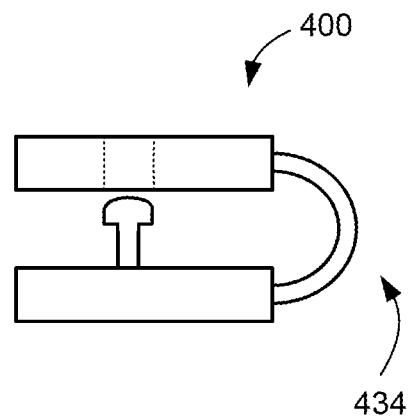
FIG. 16 is a side view of a coupler according to another embodiment of the invention.

The coupler 406 may include two separate parts—a first member 422 and a second member 424, as shown in FIG. 15. The members 422, 424 may form a pair of interconnecting discs to couple the first elongate member 402 with the second elongate member 404. The first elongate member 422 may be a circular disc 426 from which a portion or multiple portions may be protruded to form a projection portion 428. Further, the projection portion 428 may be positioned beneath the disc 426. The second member 424 may also be a circular disc 430 having or defining an opening or a hole 432 defined in the disc, for example in the center of the disc 430. The opening 420 may be concentric with the circular disc 430. The opening 420 may have dimensions, such as depth and width, in accordance with size/shape of the projection portion 428 so that the projection portion 428 may extend all the way through the opening and may be snapped/fixed tightly into/through the opening 432 when the first member 422 is pressed into the second member 424, as shown in FIG. 14. The circular disc 426 may be of same diameter as that of the circular disc 430 to facilitate fitting of the members 422, 424. In some embodiments, the projection portion is cylindrical in shape, in other embodiments it is flat with a width similar to or larger than opening 432, in still other embodiments, projection portion 428 has a cross-sectional shape somewhere between a flat shape and a circle. In some embodiments either project member 428 or opening 432 or both are have non-circular shapes (e.g. square, triangular, etc.).

Figure 13:
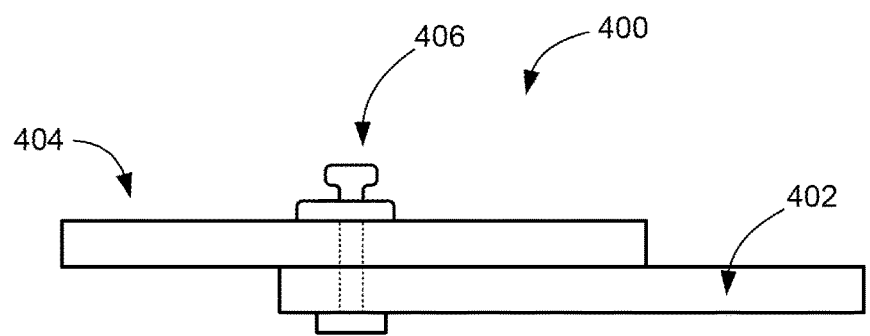
FIG. 13 is a side view of a medical device according to an embodiment of the invention.

As shown in FIG. 13, the first member 422 may be placed beneath a first end portion 408 of the first elongate member 402 such that the projection portion 428 protrudes through a pore at the first end portion 408 of the first elongate member 402. Then, a second end portion 414 of the second elongate member 404 may be placed over the first end portion 408 of the first elongate member 402 such that the projection portion 428 also emerges out through a pore at the second elongate member 404. The second member 424 may be pressed tightly over the first member 422 such that the projection portion 428 may be received in the opening 420, thereby coupling the first elongate member 402 with the second elongate member 404. In some embodiments, the projection portion 428 may include a tip portion that is wider or larger than the middle portion of the projection. The wider or larger tip portion may facilitate that coupling of the members 422 and 424.

In some embodiments, the coupler 406 may include a hinge or connection member 434 that may connect the first member 422 with the second member 424. In some embodiments, the hinge member helps prevent the members 422, 424 from getting misplaced. Also, in some embodiments, the hinge member may facilitate the coupling or associating of the members 422 and 424. The hinge 434 may be made from same materials as that of the coupler 406.

In some embodiments, the members 422, 424 of the coupler 406 may have a shape that is substantially circular. It will be recognized that alternative shapes such as oblong, elliptical, square, rectangle, or the like are also suitable. The coupler 406 may be made from a suitable biocompatible material. Examples of such materials may include, such as, but are not limited to, metals such as gold, platinum, silver, titanium, or the like; polymers such as poly(vinyl alcohol), poly(ethylene glycol), poly(N-2-hydroxypropyl methacrylamide), or the like; alloys such as stainless steel, nitinol, or the like; or any combinations thereof.

In some embodiments, a bioabsorbable material, for example a bioabsorbable polymer or a natural material may be added to the material of the coupler so that the coupler may be absorbed within the body of a patient through blood stream/other natural compositions, over a period of time after implanting the medical device within the body lumen. Examples of suitable bioabsorbable materials may include may include polymers, such as poly-L-lactide (PLLA), polyglycolide (PGA), polylactide (PLA), poly-D-lactide (PDLA), polycaprolactone, polydioxanone, polygluconate, polylactic acid-polyethylene oxide copolymers, poly(hydroxybutyrate), polyanhydride, poly(amino acids), and combinations thereof. Examples of natural materials include collagen, elastin, fibrin and other proteins as amino acids. In some embodiments, the biocompatible material may comprise ceramics or minerals, for example calcium.

In the above embodiments, the coupler may be manufactured by any suitable fabrication process that is well known in the art, for example a molding process, to form the coupler. For example, cast molding, injection molding, stereo lithography and so forth. Other manufacturing methods include, but are not limited to, machining and laser cutting.

In some embodiments, the couplers (106 or 206 or 306 or 406) described above may be temporarily or permanently attached to the elongate members that will be described in conjunction with subsequent figures.

Figure 17:
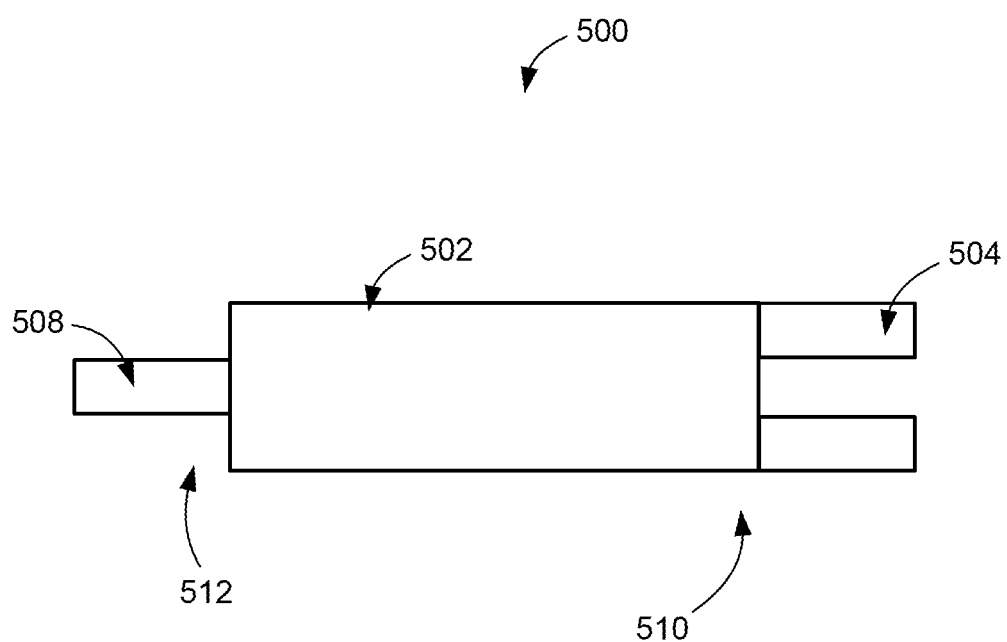
FIG. 17 is a schematic illustration of an insertion device according to an embodiment of the invention.

FIG. 17 is a schematic illustration of an insertion device according to an embodiment of the invention. As shown in FIG. 17, a delivery tool 500 is disclosed that may be provided to deliver a coupler 514 in the body of the patient. The tool 500 may include an elongate body 502, a first arm 504, a second arm 506, and an actuator 508. The arms 504, 506, and the actuator 508 may be disposed on either side of the elongate body 502. Further, the arms 504, 506 may extend from a side 510 of the elongate body 502 and may be pivotally connected to the elongate body 502. The first arm 504 may include a duct/groove to retain the first member 522 of the coupler 514. Similarly, the second arm 506 may include a duct/groove to retain the second member 524 of the coupler 514. The actuator 508 may be extended from another side 512 of the elongate body 502. In some embodiments, the delivery tool 500 may store or house multiple or more than one coupler 514. For example, the elongate body 502 may house or store more than one coupler 514. Thus, the device may be used to attach more than one coupler to the implant without removing the delivery tool from the body between the coupling of each coupler.

In some embodiments, the delivery tool 500 is inserted into the body via an abdominal incision including a laparoscopic port. In other embodiments, the delivery tool 500 may be inserted into the body of the patient though another bodily incision, such as a vaginal incision.

Figure 18:
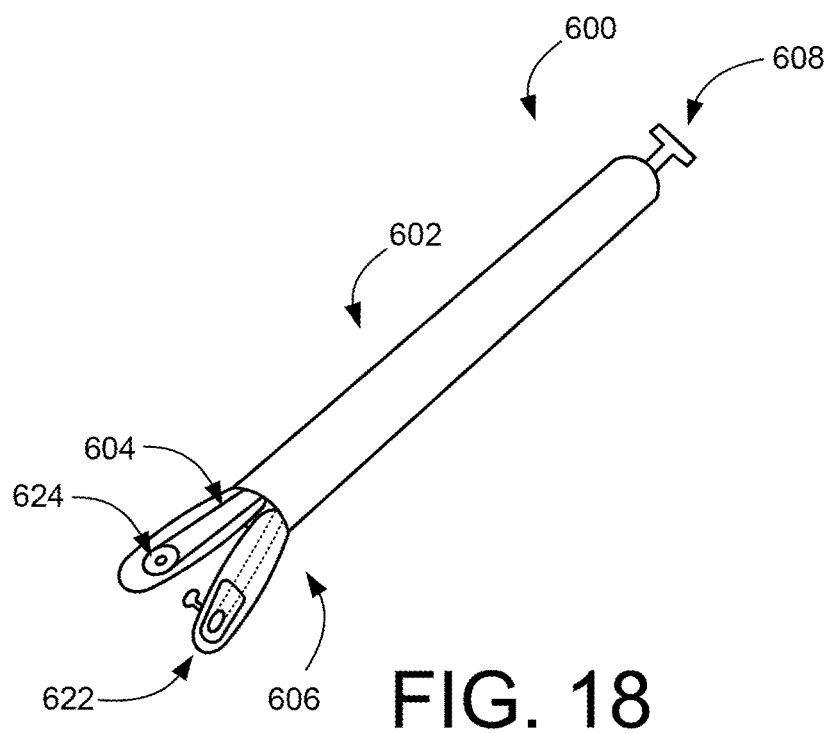
FIG. 18 is a perspective view of an insertion device according to an embodiment of the invention.
Figure 19:
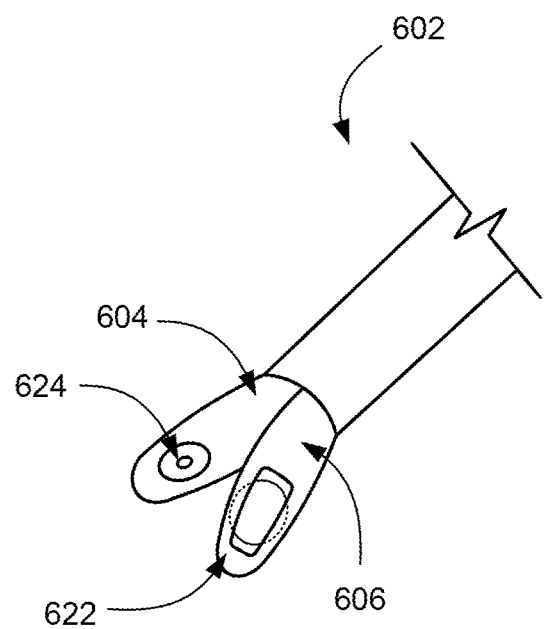
FIG. 19 is a perspective view of an end portion of the insertion device of FIG. 18.

In some embodiments, an actuator 608 of delivery device 600 may be configured to move the first arm 604 with respect to the second arm 606, as shown in FIG. 18. For example, as the actuator 608 is pushed, the arms 604, 606 may extend out from the elongate body 602 and may move towards from each other to couple members 622, 624 with each other. As the first member 622 is pressed into the second member 624, the snapped coupler 610 may be deployed in the body of the patient, thereby coupling the first elongate member 402 with the second elongate member 404 of FIG. 13. Thereafter, the actuator 608 may be pulled thereby retracting or closing the arms 604, 606. A close view of the arms 604, 606 retaining the members 622, 624 respectively is shown in FIG. 19.

Figure 20:
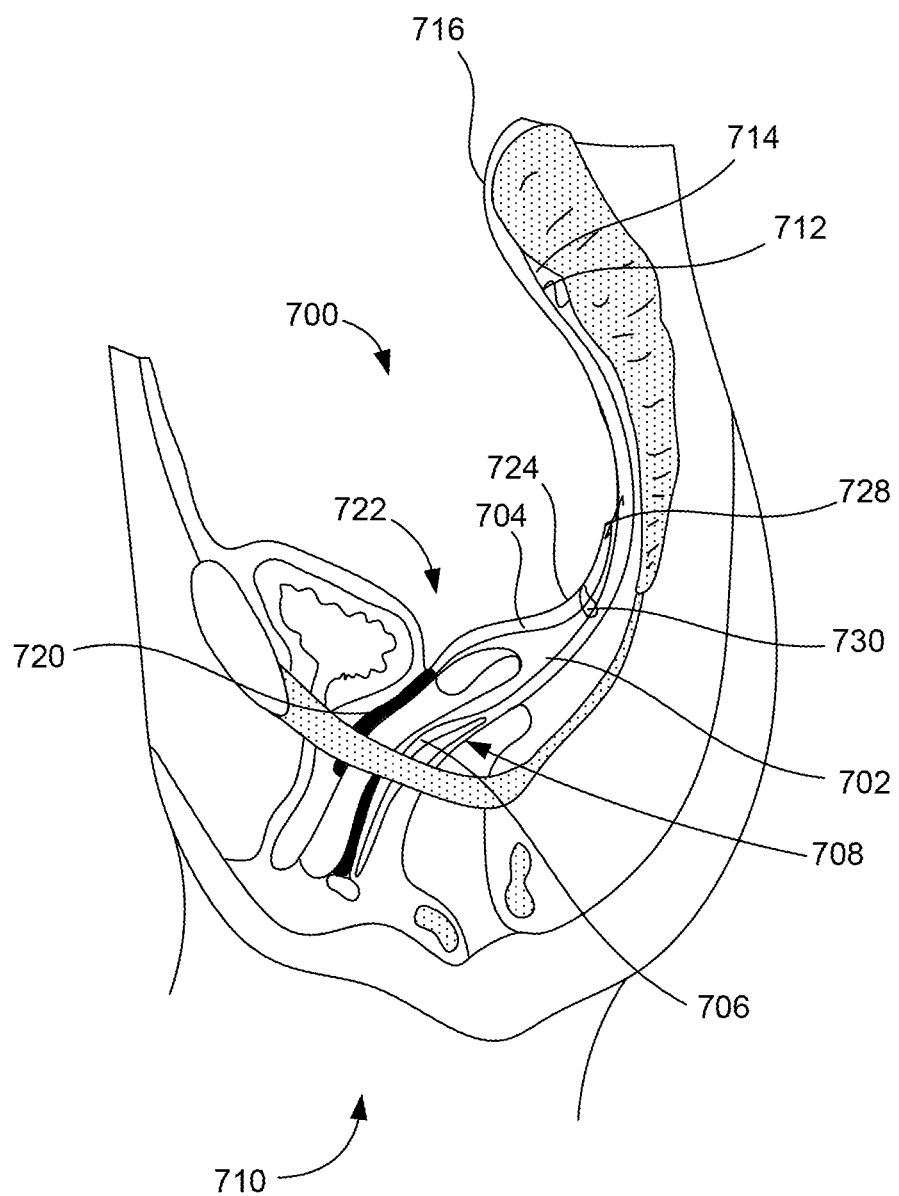
FIG. 20 schematically illustrates a medical device according to an embodiment of the invention disposed within a body of a patient.

FIG. 20 schematically illustrates a medical device according to an embodiment of the invention disposed within a body of a patient. The medical device 700 may be configured to be implanted within the body of the patient to correct POP. The medical device 700 may be structurally and functionally similar to the medical devices 100, 200, 300, so on as discussed above. The medical device 700 includes a first elongate member 702, a second elongate member 704. A first end portion 706 of the first elongate member 702 may be attached to a posterior wall 708 of the vagina 710 using a first suture (not shown). A second end portion 714 of the first elongate member 702 may be attached to a sacrum 716 or to tissue proximate the sacrum or to any other anchoring tissue of the patient using the suture 712. In some embodiments, the elongate members 702, 704 may be coupled by any other coupling member that is well known in the art, for example, a staple, etc. Then, a first end portion 720 of the second elongate member 704 may be attached to an anterior wall 722 of the vagina 710, and a second end portion 724 of the second elongate member 704 may be attached to a suitable portion of the first elongate member 702 using a second suture. The suture may be a plastic wire, a metallic wire, silk, thread, staple, or the like that may couple the elongate members 702, 704 with walls of the vagina 710.

Thereafter, a coupler 728 may be deployed in the body of the patient to connect the elongate members 702, 704 using the delivery tool 500. In case desired tension or positioning of the elongate members with respect to each other (or in case the position of the body portion being supported) is not produced or achieved, the coupler 728 may be detached and reattached to ensure desired tension in the elongate members 702, 704. As the desired tension is achieved in the elongate members 702, 704, a suture 730 may be used thereby connecting the first elongate member 702 with the second elongate member 704. Further, the coupler 706 may either be absorbed in the body of the patient or may be removed by physician after the deployment of the suture 730. This may be done to avoid discomfort to the patient due to bulkiness of the coupler 728.

Figure 21:
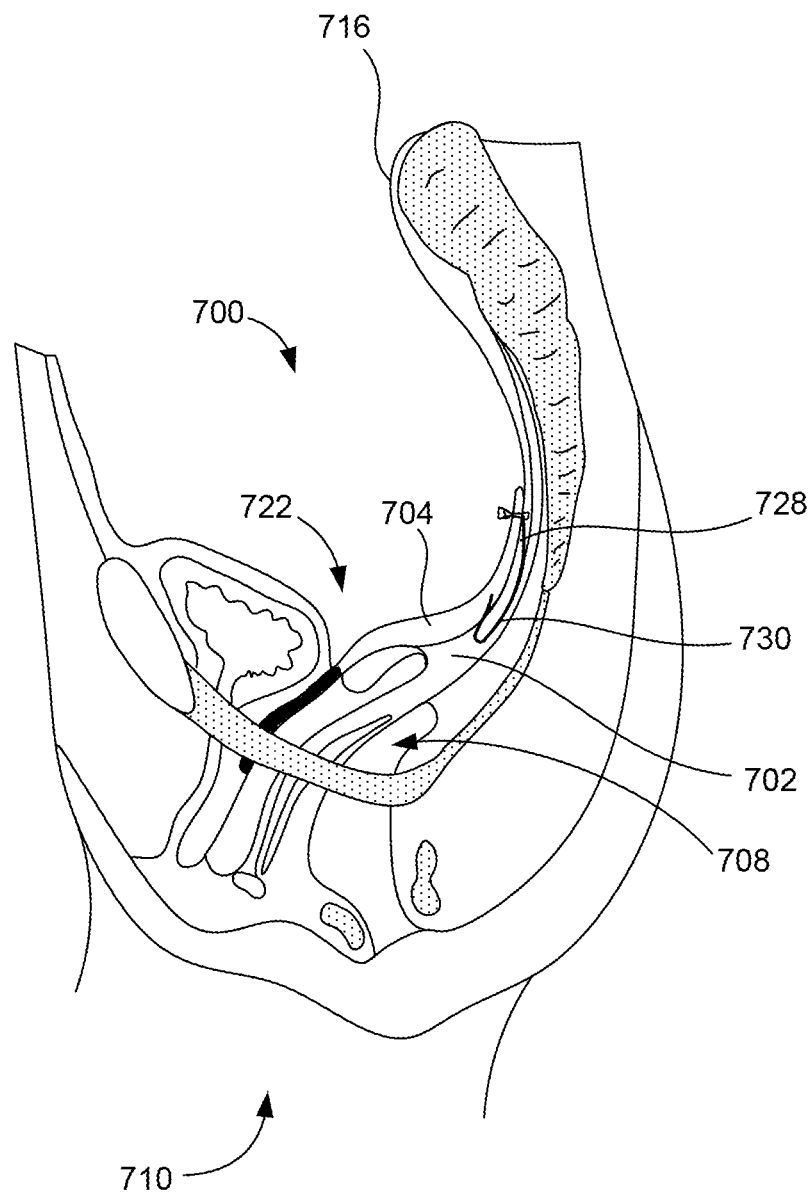
FIG. 21 schematically illustrates a medical device according to an embodiment of the invention disposed within a body of a patient.

As shown in FIG. 20, the coupler 728 may be connected anteriorly to the elongate members 702, 704 i.e. the coupler 728 may be connected to the anterior side and then may be used to pull up on the anterior side and attached to the posterior side. However, in some other embodiments, the coupler 728 may be connected posteriorly as shown in FIG. 21. The coupler 728 may be first connected to the posterior side and then may be attached to the anterior side. Thus, the coupler 728 may be used in attaching the first elongate member 702 with the second elongate member 704. Thereafter, a suture may be tied up to further ensure permanent attachment of the first elongate member 702 to the second elongate member 704.

Figure 22:
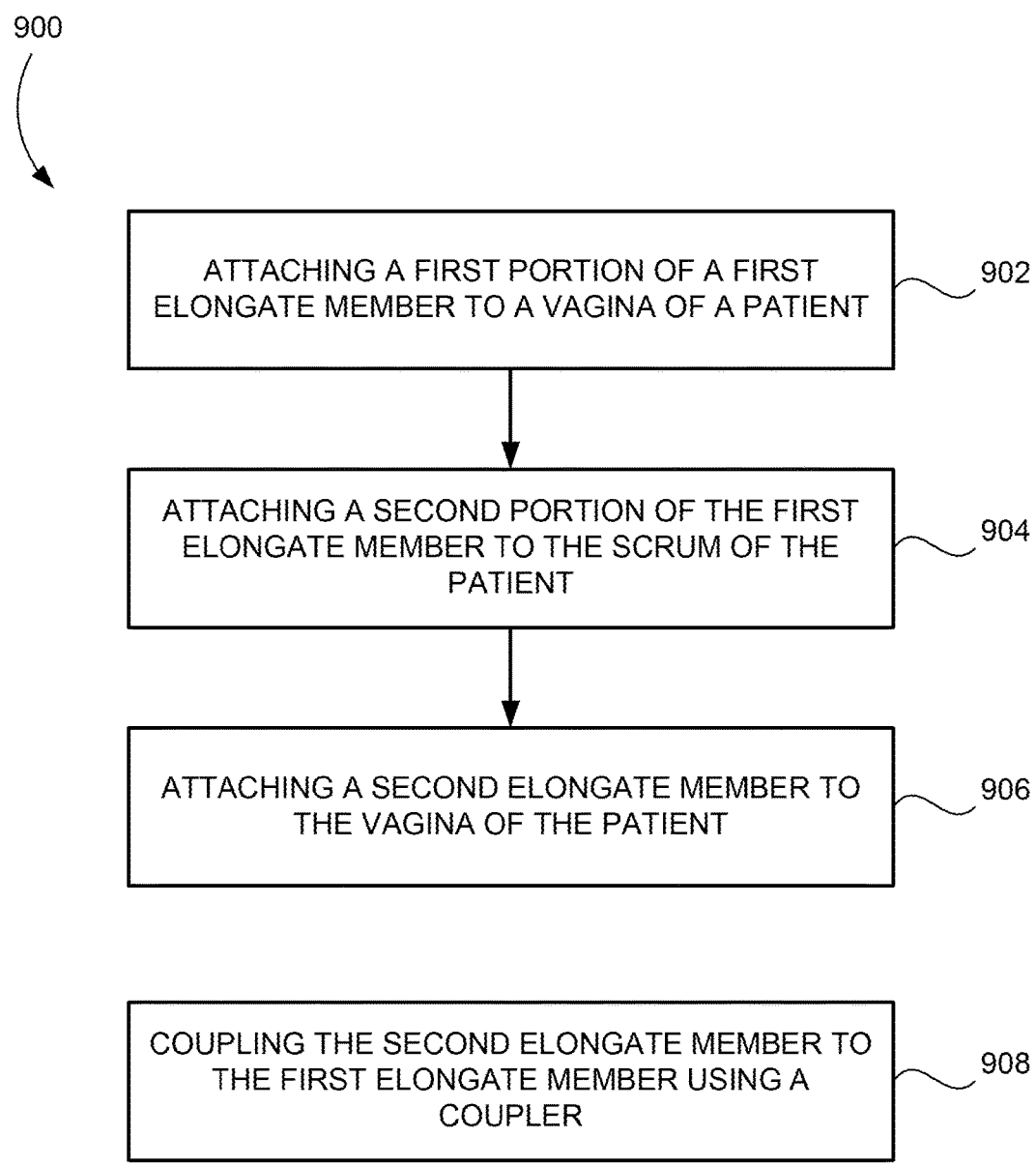
FIG. 22 is a flowchart of a method for placing an implant within a body of a patient according to an embodiment of the invention.

FIG. 22 is a flowchart illustrating a method 900 of placing an implant within a body of a patient, according to an embodiment. In some embodiments, the implant is placed within a body of a patient via an abdominal incision. In other embodiments, the implant is placed within the body of the patient via another bodily incision such as a vaginal incision. The method 900 includes attaching a first portion of a first elongate member to a vagina of a patient using a first suture, as indicated in a first step 902. In next step 904, a second portion of the first elongate member is attached to a sacrum of the patient using a second suture. A second elongate member is attached to the vagina of the patient using a third suture as depicted in a third step 906. Thereafter, the second elongate member is coupled to the first elongate member using a coupler in fourth step 908. The coupler is employed to ensure tension between the first elongate member and the second elongated member. In case, desired tension is not achieved in the elongate members, the coupler is detached and reattached. After ensuring desired tension in the elongate members, a fourth suture is introduced, thereby permanently fixing the first elongate member with the second elongate member. Thereafter, the coupler is either removed or absorbed in the body of the patient. In some embodiments, the coupler is left in the body of the patient and is not configured to be absorbed by the body of the patient.

In some embodiments, a medical device includes a first elongate member; a second elongate member; and a coupler configured to removably couple the first elongate member to the second elongate member.

In some embodiments, the coupler includes a body portion, a first extension portion extending non-parallel to the body portion, and a second extension portion extending non-parallel from the body portion. In some embodiments, the coupler includes a body portion, a first extension portion extending from the body portion, and a second extension portion extending from the body portion, the first extension portion having a bent shape, the second extension portion having a bent shape. In some embodiments, the coupler includes a body portion, a first barb member, and a second barb member, the first barb member extending toward the second barb member, the second barb member extending toward the first barb member. In some embodiments, the coupler includes a body portion, a first barb member, a second barb member, a third barb member, and a fourth barb member, the first barb member extending toward the second barb member, the second barb member extending toward the first barb member, the third barb member extending toward the fourth barb member, the fourth barb member extending toward the third barb member. In some embodiments, the coupler includes a first member and a second member the first member being configured to engage the second member to couple the first member to the second member. In some embodiments, the coupler includes a first member and a second member, the first member has a projection portion, the second member defines an opening configured to receive the projection portion of the first member to couple the first member to the second member. In some embodiments, the coupler includes a first member and a second member, the first member has a projection portion, the second member defines an opening, the projection portion of the first member being configured to extend through the first elongate member and the second elongate member and be received by the opening defined by the second member to couple the first member to the second member.

In some embodiments, the first elongate member is formed of a mesh material, the second elongate member is formed of a mesh material, the coupler includes a body portion, a first extension portion, and a second extension portion, the first extension portion configured to extend through the first elongate member and the second elongate member, the second extension member being configured to extend through the first elongate member and the second elongate member. In some embodiments, the coupler is molded. In some embodiments, the coupler is formed of at least one of a metal material and a bioabsorbable material.

In some embodiments, a method of placing a medical device into a body of a patient, the medical device including a first elongate member, a second elongate member, and a coupler, the method includes attaching a first end portion of the first elongate member to a vagina of the patient; attaching a second end portion of the first elongate member to a sacrum of the patient; attaching the second elongate member to the vagina of the patient; and coupling the second elongate member to the first elongate member using the coupler.

In some embodiments, the method includes suturing the second elongate member to the first elongate member after the coupling the second elongate member to the first elongate member using the coupler.

In some embodiments, the attaching the first end portion of the first elongate member to the vagina of the patient includes attaching the first end portion of the first elongate member to a posterior portion of the vagina of the patient.

In some embodiments, the attaching the second elongate member to the vagina of the patient includes attaching the second elongate member to an anterior portion of the vagina of the patient.

In some embodiments, the method includes tensioning the second elongate member to place the vagina in a desired position before the coupling the second elongate member to the first elongate member using the coupler.

In some embodiments, the coupling the second elongate member to the first elongate member includes passing a projection portion of a first member of the coupler through the first elongate member, through the second elongate member, and into an opening defined by a second member of the coupler.

In some embodiments, the coupling the second elongate member to the first elongate member includes inserting a delivery tool including a coupler into the body of the patient and activating the tool to dispose the coupler into the body of the patient such that the coupler couples the second elongate member to the first elongate member.

In some embodiments, a delivery tool includes an elongate body; a first arm extending from the elongate body and configured to removably retain a first member of a coupling device; a second arm extending from the elongate body and configured to removably retain a second member of a coupling device; and an actuator configured to move the first arm with respect to the second arm.

In some embodiments, the first arm is pivotally coupled to the elongate body, the second arm is pivotally coupled to the elongate body.

It should be understood that this disclosure is, in many respects, only illustrative. Changes may be made in details, particularly in matters of shape, size, and arrangement of steps, without exceeding the scope of the disclosure. This may include, to the extent that it is appropriate, the use of any of the features of one exemplary embodiment in other embodiments. The disclosure's scope is, of course, defined in the language in which the appended claims are expressed.

What is claimed is:

1. A medical device, comprising:
   a first mesh elongate member;
   a second mesh elongate member, the first mesh elongate member having a length greater than a length of the second mesh elongate member, wherein the first mesh elongate member and the second mesh elongate member are configured to be implanted within a body of a patient to treat a pelvic organ prolapse; and
   a coupler configured to removably couple the first mesh elongate member to the second mesh elongate member, the coupler including a body member, a first extension member, and a second extension member, each of the first extension member and the second extension member including a first segment extending non-parallel from a longitudinal axis of the body member, and a second segment extending back towards the body member.

2. The medical device of claim 1, wherein the first extension member of the coupler is configured to extend through the first mesh elongate member and the second mesh elongate member, and the second extension member of the coupler is configured to extend through the first mesh elongate member and the second mesh elongate member.

3. The medical device of claim 1, wherein the coupler includes a molded material.

4. The medical device of claim 1, wherein the coupler includes at least one of a metal material and a bioabsorbable material.

5. The medical device of claim 1, wherein the body member includes a first end portion and a second end portion, the first segment of the first extension member extending from the first end portion of the body member, the first segment of the second extension member extending from the second end portion of the body member.

6. The medical device of claim 1, wherein each of the first extension member and the second extension member includes a third segment disposed between the first segment and the second segment, the third segment including a curved portion.

7. The medical device of claim 6, wherein the first segment, the second segment, and the third segment of the first extension member, collectively, define a first U-shape at a first end portion of the body member, and the first segment, the second segment, and the third segment of the second extension member, collectively, define a second U-shape at a second end portion of the body member.

8. The medical device of claim 1, wherein an end portion of the first mesh elongate member is configured to overlap with an end portion of the second mesh elongate member such that an overlapping mesh portion is defined, the coupler configured to be inserted through the overlapping mesh portion, wherein, when the coupler is inserted through the overlapping mesh portion, the overlapping mesh portion is disposed between the body member and the second segment of each of the first extension member and the second extension member while the first segment of each of the first extension member and the second extension member extends through the overlapping mesh portion.

9. The medical device of claim 1, wherein the first segment of each of the first extension member and the second extension member extends perpendicularly from the longitudinal axis of the body member.

10. The medical device of claim 1, wherein the coupler is temporally used to couple the first mesh elongate member to the second mesh elongate member.

11. The medical device of claim 1, wherein the first mesh elongate member includes a first end portion and a second end portion, the first end portion of the first mesh elongate member configured to be attached to a posterior wall of a vagina, the second end portion of the first mesh elongate member configured to be attached to a sacrum or to tissue proximate the sacrum.

12. The medical device of claim 11, wherein the second mesh elongate member is configured to be attached to an anterior wall of the vagina, and the coupler is configured to anteriorly connect the first mesh elongate member to the second mesh elongate member.

13. The medical device of claim 11, wherein the second mesh elongate member is configured to be attached to an anterior wall of the vagina, and the coupler is configured to posteriorly connect the first mesh elongate member to the second mesh elongate member.

14. The medical device of claim 1, wherein the first mesh elongate member defines a plurality of pores, and each of the first extension member of the coupler and the second extension member of the coupler has a diameter less than a diameter of at least one of the plurality of pores.

15. The medical device of claim 1, wherein the coupler includes at least one of a metal material, an alloy material, and a polymer material.

16. A medical device configured to be implemented in a body of a patient to assist with correcting a pelvic organ prolapse, the medical device comprising:

a first elongate member including a first end portion and a second end portion, the first end portion of the first elongate member configured to be attached to a posterior wall of a vagina of the patient, the second end portion of the first elongate member configured to be attached to a sacrum or to tissue proximate the sacrum;

a second elongate member including a first end portion and a second end portion, the first end portion of the second elongate member configured to be attached to an anterior wall of the vagina of the patient; and a coupler configured to be inserted into a body of the patient, the coupler configured to temporally couple the second end portion of the second elongate member to a portion of the first elongate member that is disposed between the first end portion of the first elongate member and the second end portion of the first elongate member, the coupler being used to couple the first elongate member to the second elongate member after the first end portion of the elongate member is attached to the posterior wall and after the second end portion of the first elongate member is attached to the sacrum or the tissue proximate the sacrum, the coupler including a body member, a first extension member, and a second extension member, each of the first extension member and the second extension member including a first segment extending non-parallel from a longitudinal axis of the body member, a second segment extending back towards the body member, and a third segment disposed between the first segment and the second segment, the third segment including a curved portion.

17. The medical device of claim 16, wherein the body member includes a first end portion and a second end portion, the first segment of the first extension member extending from the first end portion of the body member, the first segment of the second extension member extending from the second end portion of the body member.

18. The medical device of claim 16, wherein the first segment, the second segment, and the third segment of the first extension member, collectively, define a first U-shape, and the first segment, the second segment, and the third segment of the second extension member, collectively, define a second U-shape.

* * * * *